United States Patent [19]

Yazawa

[11] Patent Number: 4,797,737
[45] Date of Patent: Jan. 10, 1989

[54] IMAGING APPARATUS FOR ENDOSCOPE

[75] Inventor: Nobuyoshi Yazawa, Tokyo, Japan

[73] Assignee: Olympus Optical Co., Ltd., Tokyo, Japan

[21] Appl. No.: 117,800

[22] Filed: Nov. 5, 1987

[30] Foreign Application Priority Data

Nov. 19, 1986 [JP] Japan ................... 61-276086

[51] Int. Cl.$^4$ .......... A61B 1/04; A61B 1/06; H04N 7/18; G11B 15/18
[52] U.S. Cl. ................... 358/98; 128/6; 360/74.1
[58] Field of Search ............ 358/98, 906, 335, 225, 358/229; 128/4, 6; 360/69, 74.1

[56] References Cited

U.S. PATENT DOCUMENTS

| 4,413,278 | 11/1983 | Feinbloom | 358/98 |
| 4,475,539 | 10/1986 | Konomura | 128/6 |
| 4,539,601 | 9/1986 | Komine | 358/335 |
| 4,590,923 | 5/1986 | Watanabe | 128/6 |
| 4,639,772 | 1/1987 | Sluyter | 358/98 |
| 4,651,202 | 3/1987 | Arakawa | 358/98 |
| 4,722,000 | 1/1988 | Chatenever | 358/98 |

Primary Examiner—Howard W. Britton
Attorney, Agent, or Firm—Frishauf, Holtz, Goodman & Woodward

[57] ABSTRACT

An imaging apparatus for an endoscope includes a TV camera which can be mounted on an eyepiece section of the endoscope, a VTR electrically connected thereto, and a manual switch formed on the TV camera to control the recording operation being performed by the VTR. When the TV camera is removed from the endoscope without the manual switch being turned, the recording operation of the VTR is stopped automatically by an ON/OFF switch.

6 Claims, 2 Drawing Sheets

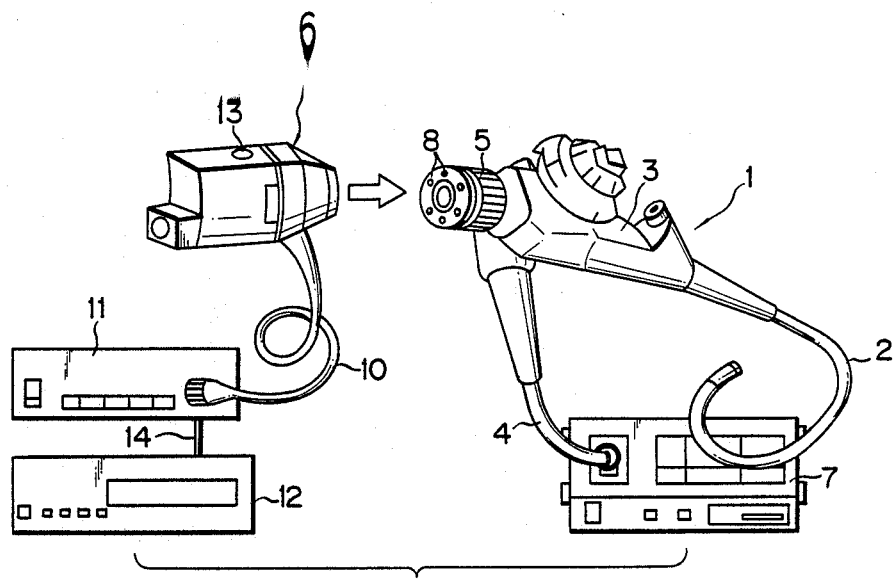
F I G. 1
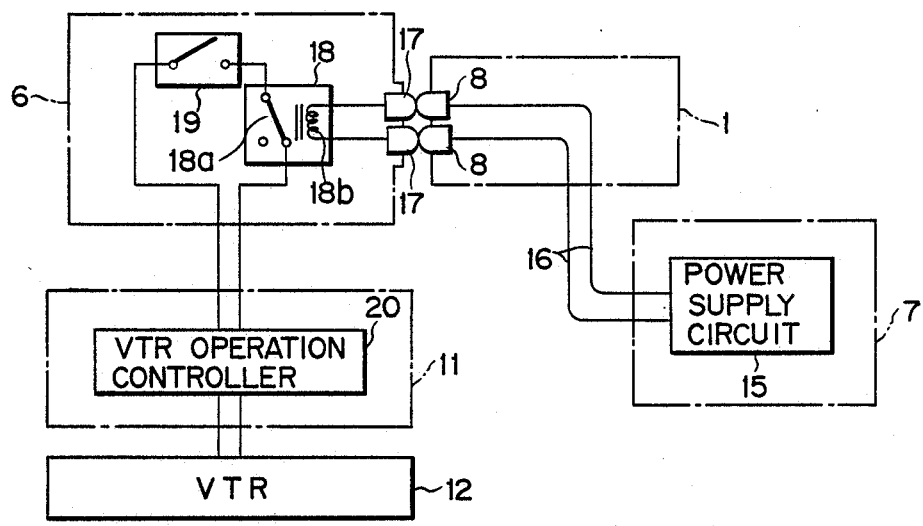
F I G. 2

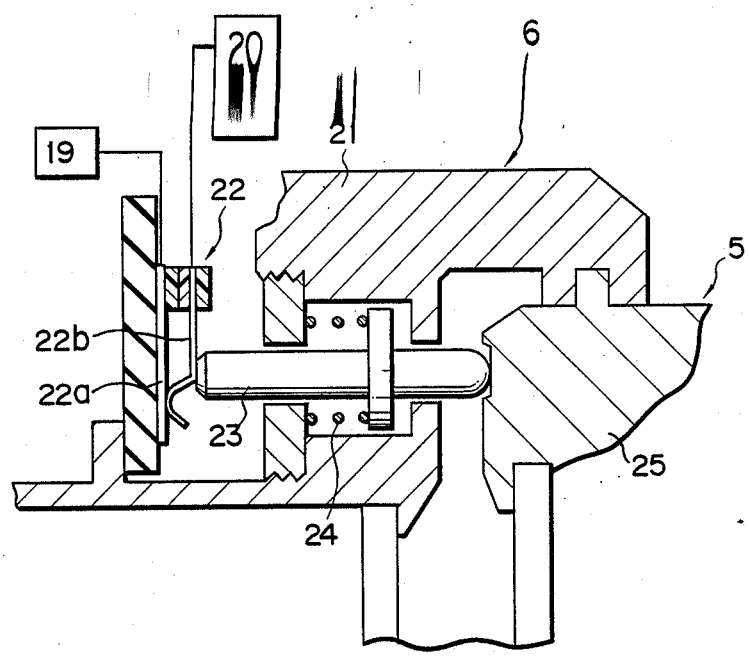
F I G. 3
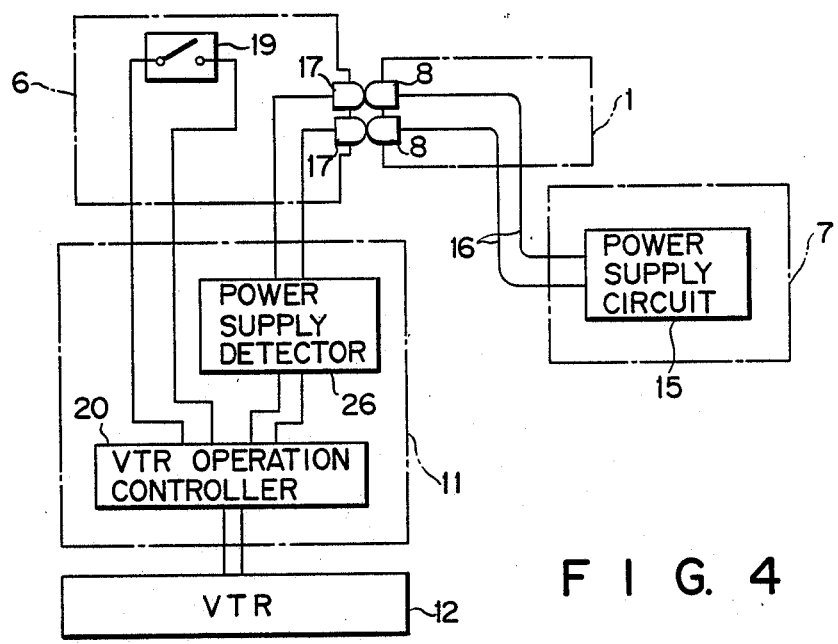
F I G. 4

IMAGING APPARATUS FOR ENDOSCOPE

BACKGROUND OF THE INVENTION

The present invention relates to an imaging apparatus for use with an endoscope.

In general, an optical endoscope includes an elongated insertion section for insertion into a body cavity, and an operation section for performing external control of the insertion section. A universal cord for connection to a light source extends from the operation section, on which is arranged an eyepiece section for enabling the operator to observe the inside of a body cavity when the insertion section is inserted therein. In addition to normal observation by the human eye, this endoscope permits observation by means of an imaging apparatus designed for use therewith. When this imaging apparatus is to be used in conjunction with the endoscope, a TV camera is mounted on the endoscope eyepiece section. An image processor processes the image signal received from the TV camera, to thereby display the resultant image on a monitor. Alternatively, a VTR controlled by a VTR operation controller can be used to record the image signal.

When the above-described conventional imaging apparatus is being used, it often happens that when the TV camera is uncoupled from the eyepiece section of the endoscope, the operator, however, forgets to stop the recording operation. The TV camera therefore continues to perform recording, unnecessarily, with the result that recording tape is wasted, and a cumbersome and time-consuming editing process must subsequently be carried out, e.g., cutting out the unnecessary part of the recording tape.

SUMMARY OF THE INVENTION

Accordingly, it is an object of the present invention to provide an imaging apparatus for use with an endoscope, which can automatically stop its recording operation if the operator has forgotten to do so.

In order to achieve the above object, there is provided according to the present invention an imaging apparatus for use with an endoscope, comprising a TV camera which can be mounted on an eyepiece section of the endoscope, a VTR electrically connected to the TV camera, a manual switch, arranged in the TV camera, for controlling the recording operation being performed by VTR, and safety means for automatically stopping the recording operation being performed by the VTR when the camera is removed from the endoscope.

According to the imaging apparatus of the present invention, if the TV has been removed from the endoscope, the recording operation being performed by the VTR is stopped automatically, if this has not been done so by the operator.

As a result, image recording is performed in an efficient manner, with unnecessary, i.e., wasteful image recording being prevented.

BRIEF DESCRIPTION OF THE DRAWINGS

FIG. 1 is a perspective view showing an imaging apparatus for use with an endoscope, according to an embodiment of the present invention, together with the endoscope;

FIG. 2 is a view illustrating an arrangement of an electrical circuit of the embodiment of FIG. 1;

FIG. 3 is a sectional view showing a part of a TV camera mounted on an eyepiece section of an endoscope according to a second embodiment of the present invention; and FIG. 4 is a view showing an arrangement of an electrical circuit according to a third embodiment of the present invention.

DETAILED DESCRIPTION OF THE PREFERRED EMBODIMENTS

As is shown in FIG. 1, endoscope 1 includes insertion section 2 for insertion into a body cavity, operation section 3 for performing external control of the insertion section, and universal cord 4 for connection to a light source and electric source unit 7. Operation section 3 of the endoscope includes eyepiece section 5 which is provided with various contacts, including current supply contacts 8, to enable signals or control currents to be transmitted to various peripheral devices via electric wires (not shown) extending from light source unit 7 into universal cord 4.

TV camera 6 of the imaging apparatus according to the present invention can be mounted detachably on eyepiece section 5 of the endoscope, and is electrically connected to camera controller 11 via camera cable 10. Camera controller 11 is also electrically connected to VTR (video tape recorder) 12, via electric cable 14, and can additionally be connected to a TV monitor (not shown). Recording operations performed by VTR 12 are controlled by switch button 13, incorporated in TV camera 6, which controls the start/cut/pause operation. More specifically, upon operation of the switch button, an operation signal is transmitted to camera controller 11, via a signal path inside the camera cable, and a VTR control signal generated therein is supplied to VTR 12, via electric cable 14, to control the recording operation carried out by the VTR.

In this embodiment, TV camera 6 can, when mounted on eyepiece section 5 of the endoscope, receive a control current from the power supply via current supply contacts 8 formed on section 5. For this purpose, TV camera 6 has electrical contacts 17 (shown in FIG. 2) formed thereon, which are designed to connect with current supply contacts 8.

As is shown in FIG. 2, in which universal cord 4 of endoscope 1 is connected to light source unit 7, a 12 V current is supplied from power supply circuit 15, which serves as the power source, to current supply contacts 8 formed on the eyepiece section, via electric wires 16 running through universal cord 4.

Manual switch 19, operated by switch button 13, and relay switch 18, connected in series therewith, are arranged inside TV camera 6. VTR operation controller 20 is housed in camera controller 11 and its operation is controlled by manual switch 19. Controller 20 is electrically connected to VTR 12, to enable it to generate a signal for controlling the operation thereof. These operations are known in the field to which the present invention pertains, and thus a detailed description thereof will be omitted.

Relay switch 18 includes ON/OFF switch 18a series-connected to manual switch 19, to serve as a safety means, and electromagnetic coil 18b parallel-connected to switch 18a. Coil 18b is electrically connected to electrical contacts 17 of TV camera 6, and when excited, attracts ON/OFF switch 18a to turn it on, as is shown in FIG. 2. When coil 18b is not excited, switch 18a is brought to an OFF position by a bias means (not shown)

for opening a circuit constituted by manual switch 19 and VTR operation controller 20.

When TV camera 6 of the imaging apparatus according to the embodiment is mounted on eyepiece section 5, current supply contacts 8 thereof and electrical contacts 17 of TV camera 6 become electrically connected to each other. As is described above, contacts 8 are connected, via wires 16, to power supply circuit 15 arranged in light source unit 7. Therefore, relay coil 18b of relay switch 18 in TV camera 6 is electrically connected to power supply circuit 15 via contacts 17. Consequently, switch 18a of relay switch 18 is turned on as shown in FIG. 2. Thereafter, switch 19 is turned on by operating switch button 13, thereby controlling VTR operation controller 20 housed in camera controller 11. VTR operation controller 20 itself controls the start/stop of the recording operation performed by VTR 12.

When TV camera 6 is uncoupled from eyepiece section 5, contacts 8 thereof and contacts 17 of TV camera 6 are electrically disconnected from each other. As a result, relay coil 18b of relay switch 18 is deenergized, and switch 18a is turned off again. Consequently, the circuit constituted by manual switch 19 and VTR operation controller 20 is opened, to thereby automatically stop the recording operation being performed by VTR 12. Therefore, even if manual switch 19 is switched to the recording position, once TV camera 6 has been uncoupled from eyepiece section 5, the recording operation being performed by VTR 12 is stopped automatically. Thus, wasteful use of tape is prevented, with the result that a cumbersome, time-consuming editing process does not have to be performed.

A second embodiment shown in FIG. 3 will now be described below.

In the second embodiment, mount 21 of TV camera 6 is mounted on mount 25 of eyepiece section 5 of the endoscope, in the axial direction thereof. Also in this embodiment, ON/OFF switch 22 constituted by a leaf spring is provided as a safety means. Switch 22 is series-connected to manual switch 19, in the same manner as in the first embodiment. Switch 22 is constituted by stationary piece 22a connected to manual switch 19, and movable piece 22b connected to VTR operation controller 20. On the other hand, movable and stationary pieces 22b and 22a can be connected to manual switch 19 and VTR operation controller 20, respectively. Normally, switch 22 is set in the OFF state, since stationary piece 22a and movable piece 22b are separated from each other due to an elastic force produced by movable piece 22b. Switch 22 can be turned on by an axially movable switch operation means, i.e., operation pin 23.

Operation pin 23 extends from mount 21 toward eyepiece section 5, and is biased by compression coil spring 24 in a direction theretoward. When TV camera 6 is not mounted on eyepiece section 5, operation pin 23 projects from mount 21. In this case, switch 22 is set in the OFF position. When, on the other hand, TV camera 6 is mounted on eyepiece section 5, operation pin 23 is pushed, by mount 25, into mount 21, thereby turning on switch 22, as shown in FIG. 3.

Therefore, when TV camera 6 is mounted on eyepiece section 5, operation pin 23 is pushed inside by mount 25 of the eyepiece section, thereby to turn on switch 22. As a result, VTR operation controller 20, housed in camera controller 11, and thus, the recording operation being performed by VTR 12, can be controlled by operating switch button 13 to control manual switch 19.

When TV camera 6 is uncoupled from eyepiece section 5, operation pin 23 is released from mount 25 and pushed by spring 24, so that it projects from mount 21. As a result, switch 22 is released from the pressing force of pin 23, and is returned to the OFF position by its own spring force. Therefore, in the event that TV camera 6 is uncoupled from eyepiece section 5 but the operator has forgotten to stop the recording operation being performed by the VTR, the recording operation will then be stopped automatically.

A third embodiment shown in FIG. 4 will now be described below.

As in the first embodiment, TV camera 6 of an imaging apparatus according to this embodiment, includes contacts 17 for enabling electrical connection to power supply circuit 15 of light source unit 7 via contacts 8 of eyepiece section 5. Contacts 17 are also connected to power supply detector 26, which serves as a safety means in this embodiment. Power supply detector 26 is arranged in camera controller 11, and is connected, independently from manual switch 19, to VTR operation controller 20, for transmitting a signal thereto. In response to the signal from power supply detector 26, VTR operation controller 20 controls the recording operation performed by VTR 12, by means of manual switch 19, when electrical contacts 17 are electrically connected to current supply contacts 8. When the contacts are not electrically connected to each other, VTR operation controller 20 automatically stops the recording operation being performed by VTR 12. Power supply detector 26 and VTR operation controller 20 described above are known in the field of the present invention, and thus a detailed description thereof will be omitted.

When TV camera 6 of the imaging apparatus according to this embodiment is mounted on eyepiece section 5, contacts 8 and contacts 17 become electrically connected to each other, so that power supply detector 26 supplies a power supply signal to VTR operation controller 20. As a result, the recording operation performed by VTR 12 can be controlled by operating manual switch 19, using switch button 13 of TV camera 6.

When TV camera 6 is uncoupled from eyepiece section 5, power supply detector 26 detects that the TV camera has thus been removed from endoscope 1 and supplies an OFF signal to VTR operation controller 20 via contacts 17, thereby automatically stopping the recording operation being performed by VTR 12.

Therefore, even if TV camera 6 is removed from endoscope 1, without manual switch 19 being turned off, the recording operation being performed by VTR 12 can still be reliably stopped. This ensures the recording only of what is required to be recorded, thereby eliminating wasteful use of recording tape and the need subsequently to carry out a cumbersome, time-consuming editing process.

The present invention is not limited to the above embodiments, and various changes and modifications may be made within the spirit and scope thereof.

What is claimed is:

1. An imaging apparatus for an endoscope, comprising:
   a TV camera which can be mounted on an eyepiece section of the endoscope;
   a VTR electrically connected to said TV camera;

a manual switch, arranged in said TV camera, for controlling a recording operation performed by said VTR; and safety means for automatically stopping the recording operation being performed by said VTR when said camera is removed from the endoscope.

2. An apparatus according to claim 1, further comprising:

a camera controller including a VTR operation controller electrically connectable between said TV camera and said VTR, said VTR operation controller being controlled by said manual switch.

3. An apparatus according to claim 2, further comprising:

a power supply, current supply contacts formed on an eyepiece section of the endoscope and connected to said power supply, and electrical contacts formed on said TV camera and adapted to be electrically connected to said current supply contacts of said eyepiece section, and in which said safety means is connected to said electrical contacts and has a power supply detector for controlling an operation being performed by said VTR operation controller.

4. An apparatus according to claim 2, wherein said safety means comprises an ON/OFF switch series-connected with said manual switch.

5. An apparatus according to claim 4, further comprising:

a power supply, current supply contacts formed on said eyepiece section of the endoscope and connected to said power supply, electrical contacts formed on said TV camera and adapted to be electrically connected to said current supply contacts of said eyepiece section when said TV camera is mounted on said eyepiece section, and a relay coil which is connected to said electrical contacts for controlling switching of said ON/OFF switch.

6. An apparatus according to claim 4, further comprising:

a mount section formed on said TV camera and adapted to be mounted on an endoscope; switch operation means which is formed on said mount section and is capable of moving in an axial direction thereof; and spring means, formed on said mount section, for pushing aaid switch operation means in a direction toward the endoscope, said switch operation means including means for turning on said ON/OFF switch when said TV camera is mounted on the endoscope, and for turning off said ON/OFF switch when said TV camera is removed from the endoscope.

* * * * *